(12) United States Patent
Koike et al.

(10) Patent No.: US 8,650,039 B2
(45) Date of Patent: Feb. 11, 2014

(54) MEDICAL SERVICE SUPPORT SYSTEM, MEDICAL SERVICE SUPPORT METHOD AND COMPUTER READABLE MEDIUM

(75) Inventors: Kazumi Koike, Saitama (JP); Kunimasa Shimizu, Tokyo (JP); Takayoshi Kiuchi, Tokyo (JP); Goro Miura, Tokyo (JP); Kenji Sawada, Tokyo (JP); Koichiro Miyazaki, Tokyo (JP)

(73) Assignee: Fujifilm Corporation, Tokyo (JP)

(*) Notice: Subject to any disclaimer, the term of this patent is extended or adjusted under 35 U.S.C. 154(b) by 284 days.

(21) Appl. No.: 12/577,123

(22) Filed: Oct. 9, 2009

(65) Prior Publication Data

US 2010/0094647 A1    Apr. 15, 2010

(30) Foreign Application Priority Data

Oct. 9, 2008    (JP) .................................. 2008-262800

(51) Int. Cl.
G06Q 10/00 (2012.01)
G06Q 50/00 (2012.01)

(52) U.S. Cl.
USPC ............................................................. 705/2

(58) Field of Classification Search
USPC ......................................................... 705/2, 3
See application file for complete search history.

(56) References Cited

U.S. PATENT DOCUMENTS

| | | | |
|---|---|---|---|
| 2004/0107119 A1 | 6/2004 | Ohishi | |
| 2005/0027197 A1* | 2/2005 | Segawa et al. | 600/463 |
| 2005/0177394 A1* | 8/2005 | Hosoya et al. | 705/2 |
| 2006/0144942 A1* | 7/2006 | Evans et al. | 235/435 |
| 2007/0067189 A1* | 3/2007 | Boris et al. | 705/3 |
| 2007/0299696 A1* | 12/2007 | Matsubara et al. | 705/3 |
| 2009/0048874 A1* | 2/2009 | Sasano | 705/3 |
| 2009/0063195 A1* | 3/2009 | Araki et al. | 705/3 |

FOREIGN PATENT DOCUMENTS

| | | |
|---|---|---|
| JP | 06-274472 A | 9/1994 |
| JP | 2002-065642 A | 3/2002 |
| JP | 2002-269232 A | 9/2002 |
| JP | 2003-323493 A | 11/2003 |
| JP | 2004-178406 A | 6/2004 |
| JP | 2007-287027 A | 11/2007 |
| JP | 2007-328740 A | 12/2007 |
| WO | WO 2007/116899 A1 | 10/2007 |
| WO | WO 2008/038614 A1 | 4/2008 |

OTHER PUBLICATIONS

Japanese Office Action dated Sep. 25, 2012 with partial English translation thereof.

* cited by examiner

*Primary Examiner* — John Pauls
*Assistant Examiner* — Trang Nguyen
(74) *Attorney, Agent, or Firm* — McGinn Intellectual Property Law Group, PLLC (57) ABSTRACT

A medical service support system includes: a first input unit that inputs first patient information on a patient in carrying out a medical examination of the patient; a second input unit that inputs second patient information on the patient in executing, to the patient, a pretreatment of an inspection being ordered according to a medical examination result of the patient; a memory that stores the first patient information inputted by the first input unit and the second patient information inputted by the second input unit; a consistency judging unit that judges match or mismatch of respective common items contained in both of the first patient information and the second patient information stored in the memory, by comparing the first patient information with the second patient information for each common item; and a display unit that displays a consistency judgment result by the consistency judging unit.

18 Claims, 11 Drawing Sheets

Basic Patient Information

Name: XXXX
Age: ΔΔ
Sex: YY
Inspection assortment:
 Upper gastrointestinal endoscopy
Past history: Glaucoma
Taking medicine: Medicine A

FIG. 5

| Basic Patient Information |

Name: XXXX
Age: ΔΔ
Sex: YY

Inspection assortment:
 Upper gastrointestinal endoscopy

Past history: Glaucoma
Taking medicine: Medicine A

| Pretreatment Patient Information |

Name:
Age:
Sex:
Inspection assortment:
Submission of written agreement on the inspection:
Presence or absence of food and drink on the day:

Past history:
Taking medicine:
The number of days of suspended medicine taking:

Kind of pretreatment medicine:
Dose:
Kind of injections:
Dose:

FIG. 6

| Basic Patient Information | Pretreatment Patient Information | Consistency |

Name: XXXX
Age: ΔΔ
Sex: YY

Name: XXXX
Age: ΔΔ
Sex: YY

Consistent
Consistent
Consistent

Inspection assortment:
 Upper gastrointestinal endoscopy

Inspection assortment:
 Upper gastrointestinal endoscopy
Written agreement on the inspection: Submitted
Food and drink on the day: No Consistent Past history: Glaucoma
Taking medicine: Medicine A Past history: Diabetes mellitus
Taking medicine: Medicine A
The number of days of suspended medicine taking:
 3 days

Kind of pretreatment medicine: Medicine B
Dose: OOml
Kind of injections: Medicine C
Dose: XX A Inconsistent
Consistent

FIG. 7

| Previous Inspection Information | Basic Patient Information | Pretreatment Patient Information | Consistency |
|---|---|---|---|
| Name: XXXX<br>Age: ΔΔ<br>Sex: YY | Name: XXXX<br>Age: ΔΔ<br>Sex: YY | Name: XXXX<br>Age: ΔΔ<br>Sex: YY | Consistent<br>Consistent<br>Consistent |
| Inspection assortment:<br>  Upper gastrointestinal endoscopy<br>Inspection method: Nasal endoscope<br>Insertion region: Right nostril<br>Posture: Sitting position | Inspection assortment:<br>  Upper gastrointestinal endoscopy | Inspection assortment:<br>  Upper gastrointestinal endoscopy | Consistent |
|  |  | Written agreement on the inspection: Submitted<br>Food and drink on the day: No |  |
| Past history: Diabetes mellitus<br>Taking medicine: Medicine A | Past history: Glaucoma<br>Taking medicine: Medicine A | Past history: Diabetes mellitus<br>Taking medicine: Medicine A<br>The number of days of suspended medicine taking: 3 days | Inconsistent<br>Consistent |
|  |  | Kind of pretreatment medicine: Medicine B<br>Dose: OOml<br>Kind of injections: Medicine C<br>Dose: XX A |  |

|  | PRETREATMENT MEDICINE | | INJECTIONS | |
| --- | --- | --- | --- | --- |
|  | KIND | DOSE | KIND | DOSE |
| DIABETES MELLITUS | MEDICINE B | OOml | MEDICINE D | XXV |
| ΔΔ DISEASE |  |  |  |  |
| YY DISEASE |  |  |  |  |

FIG. 11

|  | CONTRAINDICATION MEDICINE | NUMBER OF DAYS OF SUSPENDED MEDICINE TAKING |
| --- | --- | --- |
| UPPER GASTROINTESTINAL ENDOSCOPY | MEDICINE A | 7 DAYS |
| OO INSPECTION |  |  |
| XX INSPECTION |  |  |

FIG. 12

| Basic Patient Information | Pretreatment Patient Information | Consistency | Inspection Can/cannot | Reason |
|---|---|---|---|---|
| Past history: Glaucoma | Past history: Diabetes mellitus | Inconsistent | Cannot | Past history is different |

Contraindication Information

| | | | | |
|---|---|---|---|---|
| Contraindication medicine: Medicine A | Taking medicine: Medicine A | | Cannot | Comes under contraindication medicine |
| The number of days of suspended medicine taking: 7 days | The number of days of suspended medicine taking: 3 days | | Cannot | The number of days of suspended medicine taking is insufficient |

Proper Treatment Information

| | | | | |
|---|---|---|---|---|
| Kind of pretreatment medicine: Medicine B | Kind of pretreatment medicine: Medicine B | | Can | |
| Dose: OOml | Dose: OOml | | Can | |
| Kind of injections: Medicine D | Kind of injections: Medicine C | | Cannot | The injections are not proper |
| Dose: XX V | Dose: XX A | | Cannot | The dose is not proper |

MEDICAL SERVICE SUPPORT SYSTEM, MEDICAL SERVICE SUPPORT METHOD AND COMPUTER READABLE MEDIUM

CROSS-REFERENCE TO RELATED APPLICATIONS

This application is based on and claims priority under 35 USC 119 from Japanese Patent Application No. 2008-262800 filed on Oct. 9, 2008; the entire of which are incorporated herein by reference.

BACKGROUND

1. Technical Field

This invention relates to a medical service support system which supports services carried out at medical institutions, a method for supporting medical service and a computer readable medium.

2. Related Art

At medical institutions, endoscopy and the like various inspections are executed to patients, and various medical services are present until these inspections are executed. Typically, a patient who visited a hospital for a medical examination firstly fills an inquiry card with his or her name, age, symptom, past history, taking medicines and the like, and a doctor in charge of out-patient examinations examines the patient by referring to the entered inquiry card. Thereafter, inspections required for the patient are ordered based on the examined results. The patient information obtained by the out-patient examination is recorded on a sheet of paper or stored as electronic data in a server or the like memory.

The inspection is generally carried out at the time and date different from the out-patient examination, and a pretreatment is carried out prior to the execution of the inspection. The pretreatment is generally carried out by a nurse, and the nurse checks name, age, past history, taking medicines and the like of the patient and verifies presentation of an inspection agreement. The patient information including this information and information on the pretreatment to be executed are recorded on a sheet of paper or stored as electronic data in a server or the like memory.

Thereafter, whether or not the inspection is carried out is finally judged by the doctor who executes the inspection based on the patient information so far obtained, but is generally judged based on the patient information obtained in the close pretreatment.

In order to alleviate the burden which is imposed when the information filled in an inquiry card are stored as electronic data in the medical services as described in the above, there has been proposed a medical information management device in which inquiry results corresponding to the inquiry items are prepared by obtaining execution information from a data base which keeps records of the execution information on medical actions carried out upon patients (cf. Patent Reference 1 (JP-A-2007-328740 corresponding to US-A-2007/299696)). Also, in order to carryout comparison of a patient himself or herself with the patient information quickly and certainly, there has also been proposed a medical inspection system in which patient information is stored in advance, the patient information is readout from the retrieved information peculiar to the patient, and thereby carry out verification of the patient information (cf. Patent Reference 2 (JP-A-2002-065642)). In addition, there has also been proposed a medical service support system in which pretreatment information is inputted real time, and this pretreatment information is used in the next inspection (cf. Patent Reference 3 (JP-A-2004-178406 corresponding to US-A-2004-107119)).

When whether or not an inspection should be carried out is judged by relying on one patient information, artificial mistakes such as report errors on past history and the like and record errors on patient information and the like are apt to be missed, so that there is a possibility of inhibiting execution of a proper inspection. In addition, each of the above-mentioned techniques of Patent References 1 to 3 does not apply both of the patient information obtained by out-patient examination and the patient information obtained by pretreatment to the judgment of whether or not an inspection should be carried out.

SUMMARY

Illustrative aspects of the present invention provides a medical service support system which enables proper execution of inspections by effectively using patient information, a method for supporting medical service and a computer readable medium storing a program causing the computer to execute a process for supporting medical service.

(1) According to an aspect of the invention, medical service support system includes: a first input unit that inputs first patient information on a patient in carrying out a medical examination of the patient; a second input unit that inputs second patient information on the patient in executing, to the patient, a pretreatment of an inspection being ordered according to a medical examination result of the patient; a memory that stores the first patient information inputted by the first input unit and the second patient information inputted by the second input unit; a consistency judging unit that judges match or mismatch of respective common items contained in both of the first patient information and the second patient information stored in the memory, by comparing the first patient information with the second patient information for each common item; and a display unit that displays a consistency judgment result by the consistency judging unit.

According to the above-mentioned medical service support system, attention of a person who executes the inspection can be wakened by judging match or mismatch of respective items of common items between the first patient information which is inputted when a medical examination is carried out and the second patient information which is inputted when a pretreatment is carried out, and displaying the judgment results. By this, proper execution of the inspection becomes possible.

(2) According to the medical service support system of (1), the display unit may display the first patient information, the second patient information, and the match or mismatch of the respective common items judged by the consistency judging unit. And the display unit may change a display mode of an item judged mismatch from a display mode of an item complementary to both of the first patient information and the second patient information.

According to the above-mentioned medical service support system, mismatched items among common items between the first patient information and the second patient information are as clear as daylight and therefore contribute to the attention awaking of a person who executes the inspection.

(3) According to the medical service support system according of (1), the display unit may only display items judged mismatch by the consistency judging unit, regarding the common items among the first patient information and the second patient information, and the mismatches.

According to the above-mentioned medical service support system, mismatched items among common items between the first patient information and the second patient information are as clear as daylight and therefore contribute to the attention awaking of a person who executes the inspection.

(4) According to the medical service support system of (1), the medical service support system may further include: an inspectability judging unit that judges whether or not the inspection is allowed to be executed. The inspectability judging unit may judge whether or not the inspection is allowed to be executed, in the case of a presence of one or more items judged mismatch by the consistency judging unit, regarding the common items among the first patient information and the second patient information. The display unit may further display an inspectability judgment result by the inspectability judging unit.

According to the above-mentioned medical service support system, artificial errors in judging whether or not the inspection should be executed can be avoided. By this, proper execution of the inspection becomes possible.

(5) According to the medical service support system according of (4), at least the second patient information may include past history of the patient and information on the pretreatment. The memory may store a proper treatment information table which keeps proper treatment information on the pretreatment of the inspection associated with a disease name. The inspectability judging unit may retrieve proper treatment information which corresponds to the past history of the second patient information, by referring to the proper treatment information table. And the inspectability judging unit may judge whether or not the inspection is allowed to be executed when the pretreatment information of the second patient information does not come under the retrieved proper treatment information.

According to the above-mentioned medical service support system, artificial errors in judging whether or not the inspection should be executed can be avoided. By this, proper execution of the inspection becomes possible.

(6) According to the medical service support system of (4), at least the second patient information may include medicine taking information of the patient and kind of the inspection. The memory may store a contraindication information table which keeps contraindication information on the drug associated with the kind of the inspection. The inspectability judging unit may retrieve contraindication information which corresponds to the kind of inspection of the second patient information, by referring to the contraindication information table. And the inspectability judging unit may judge whether or not the inspection is allowed to be executed when the medicine taking information of the second patient information comes under the retrieved contraindication information.

According to the above-mentioned medical service support system, artificial errors in judging whether or not the inspection should be executed can be avoided. By this, proper execution of the inspection becomes possible.

(7) According to the medical service support system of (1), the memory may store information on at least one of inspections executed in the past to the patient. And the display unit may further display the inspection information recorded in the memory.

According to the above-mentioned medical service support system, whether or not the inspection should be executed can be judged based on more many patient information. By this, proper execution of the inspection becomes possible.

(8) According to another aspect of the invention, a method for supporting medical service includes: storing in a memory, first patient information which is inputted in carrying out a medical examination of a patient; storing in the memory, a second patient information which is inputted in executing, to the patient, a pretreatment of an inspection ordered according to a medical examination result; judging match or mismatch of respective common items contained in both of the first patient information and the second patient information stored in the memory, by comparing the first patient information with the second patient information for each common item; and displaying a consistency judgment result by the judgment.

(9) According to the method for supporting medical service of (8), the displaying step may include displaying the first patient information, the second patient information, and the judged match or mismatch of the respective common items. And the displaying step may includes changing a display mode of an item judged mismatch from a display mode of an item complementary to both of the first patient information and the second patient information.

(10) According to the method for supporting medical service of (8), the displaying step may include only displaying items judged mismatch, regarding the common items among the first patient information and the second patient information, and the mismatches.

(11) According to the method for supporting medical service of (8), the method may further include: judging whether or not the inspection is allowed to be executed. The judgment as to whether or not the inspection is allowed to be executed may be performed, in the case of a presence of one or more items judged mismatch, regarding the common items among the first patient information and the second patient information. And the displaying step may include displaying an inspectability judgment result of the judgment as to whether or not the inspection is allowed to be executed.

(12) According to the method for supporting medical service of (11), at least the second patient information may include past history of the patient and information on the pretreatment. The memory may store a proper treatment information table which keeps proper treatment information on the pretreatment of the inspection associated with a disease name. The method may further include: retrieving proper treatment information which corresponds to the past history of the second patient information, by referring to the proper treatment information table. And the judgment as to whether or not the inspection is allowed to be executed may be performed when the pretreatment information of the second patient information does not come under the retrieved proper treatment information.

(13) According to the method for supporting medical service of (11), at least the second patient information may include medicine taking information of the patient and kind of the inspection. The memory may store a contraindication information table which keeps contraindication information on the drug associated with the kind of the inspection. The method may further include: retrieving contraindication information which corresponds to the kind of inspection of the second patient information, by referring to the contraindication information table. And the judgment as to whether or not the inspection is allowed to be executed may be performed when the medicine taking information of the second patient information comes under the retrieved contraindication information.

(14) According to the method for supporting medical service of (8), the memory may store information on at least one of inspections executed in the past to the patient. And the displaying step may include displaying the inspection information recorded in the memory.

(15) According to another aspect of the invention, a computer readable medium storing a program causing the computer to execute a process for supporting medical service, the process includes: storing in a memory, first patient information which is inputted in carrying out a medical examination of a patient; storing in the memory, a second patient information which is inputted in executing, to the patient, a pretreatment of an inspection ordered according to a medical examination result; judging match or mismatch of respective common items contained in both of the first patient information and the second patient information stored in the memory, by comparing the first patient information with the second patient information for each common item; and displaying a consistency judgment result by the judgment.

According to the above-mentioned methods and the computer readable medium, attention of a person who executes the inspection can be wakened by judging match or mismatch of respective items of common items between the first patient information which is inputted when a medical examination is carried out and the second patient information which is inputted when a pretreatment is carried out, and displaying the judgment results. By this, proper execution of the inspection becomes possible.

DETAILED DESCRIPTION

Figure 1:
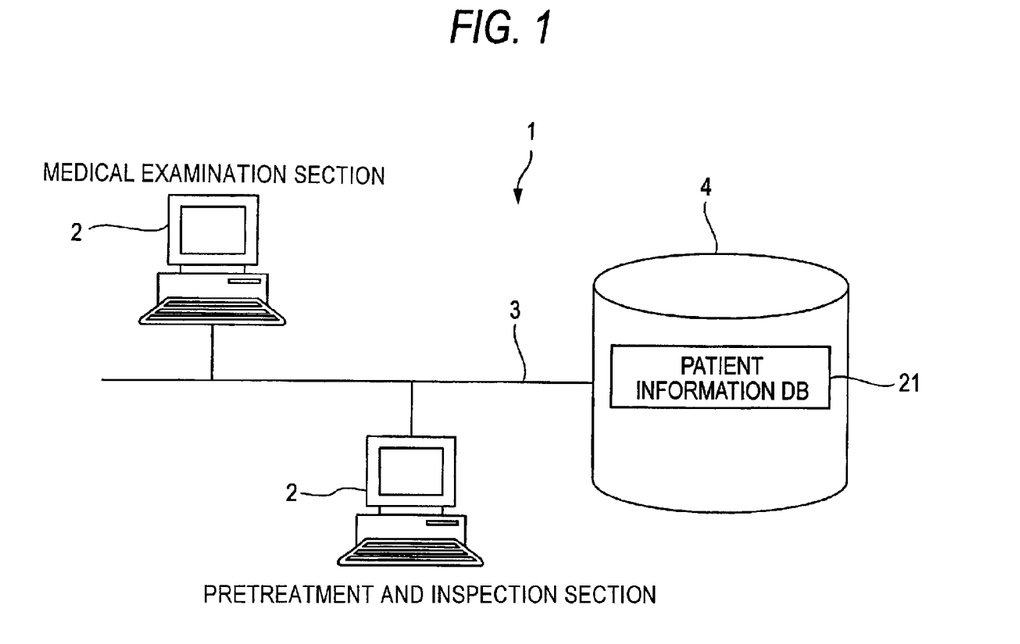
FIG. 1 is a block diagram showing schematic construction of an example of a medical service support system, for use in the explanation of an embodiment of the invention.

The following describes exemplary embodiments of the invention with reference to drawings. FIG. 1 is a block diagram showing schematic construction of an example of a medical service support system, for use in the explanation of an embodiment of the invention.

As shown in FIG. 1, the medical service support system 1 is a system for supporting a medical service in executing, to a patient, an inspection ordered for the patient based on a medical examination result. This medical service support system 1 is equipped with a PC (Personal Computer) 2 for each section of at least a medical examination section and a pretreatment and inspection section and equipped with a server or the like memory 4 which is connected with these PC 2 via a LAN (Local Area Network) or the like network 3.

Figure 2:
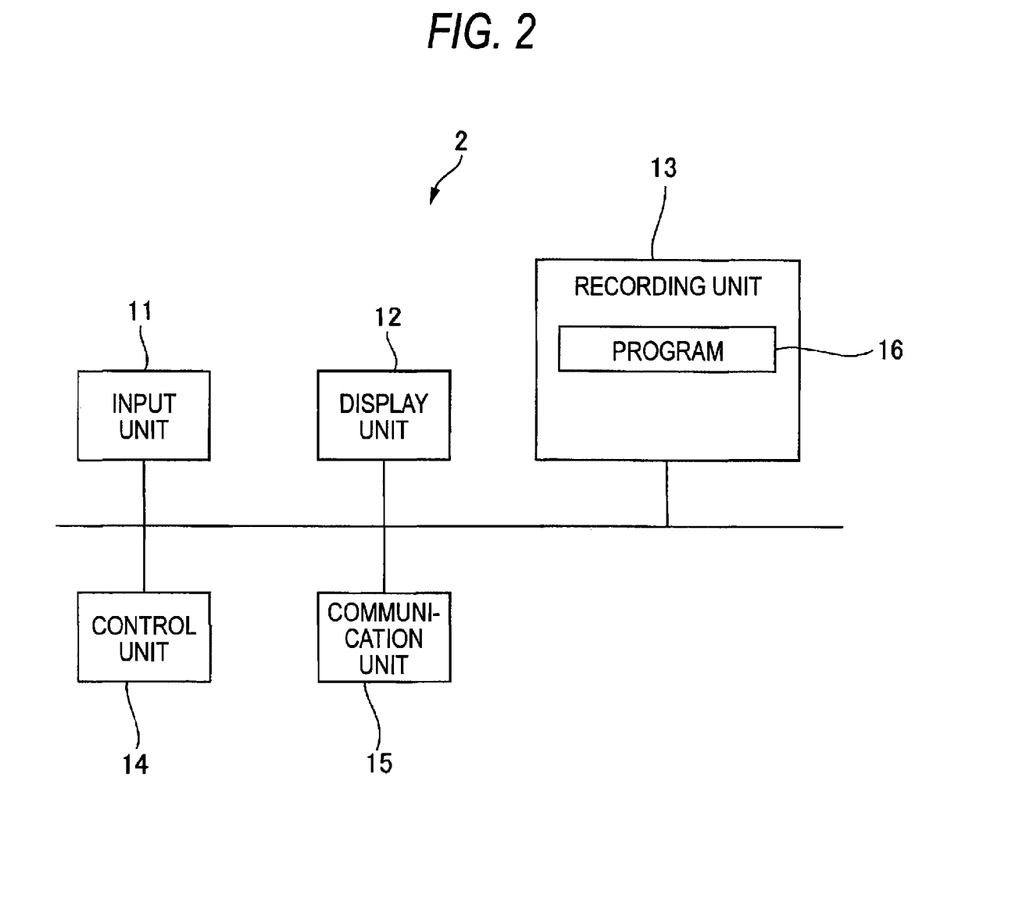
FIG. 2 is a block diagram showing schematic construction of each PC contained in the medical service support system of FIG. 1.

FIG. 2 is a block diagram showing schematic construction of each PC contained in the medical service support system of FIG. 1. The PC 2 is equipped with an input unit 11 constituted from a keyboard or the like, a display unit 12 constituted from a monitor or the like, a recording unit 13 constituted from an HDD or the like, a control unit 14 constituted from a CPU or the like, a communication unit 15 constituted from a network I/F or the like for connecting to the network 3, and the like. A medical service support program 16 is enclosed in the recording unit 13. This program 16 is loaded on the control unit 14 and makes the PC 2 to execute a predetermined treatment in concert with the above-mentioned respective elements 11 to 15.

The memory 4 stores a patient information data base 21. This patient information data base 21 records, for example, the ID given to each patient by relating it to the name, age, sex and the like patient information of the patient.

Figure 3:
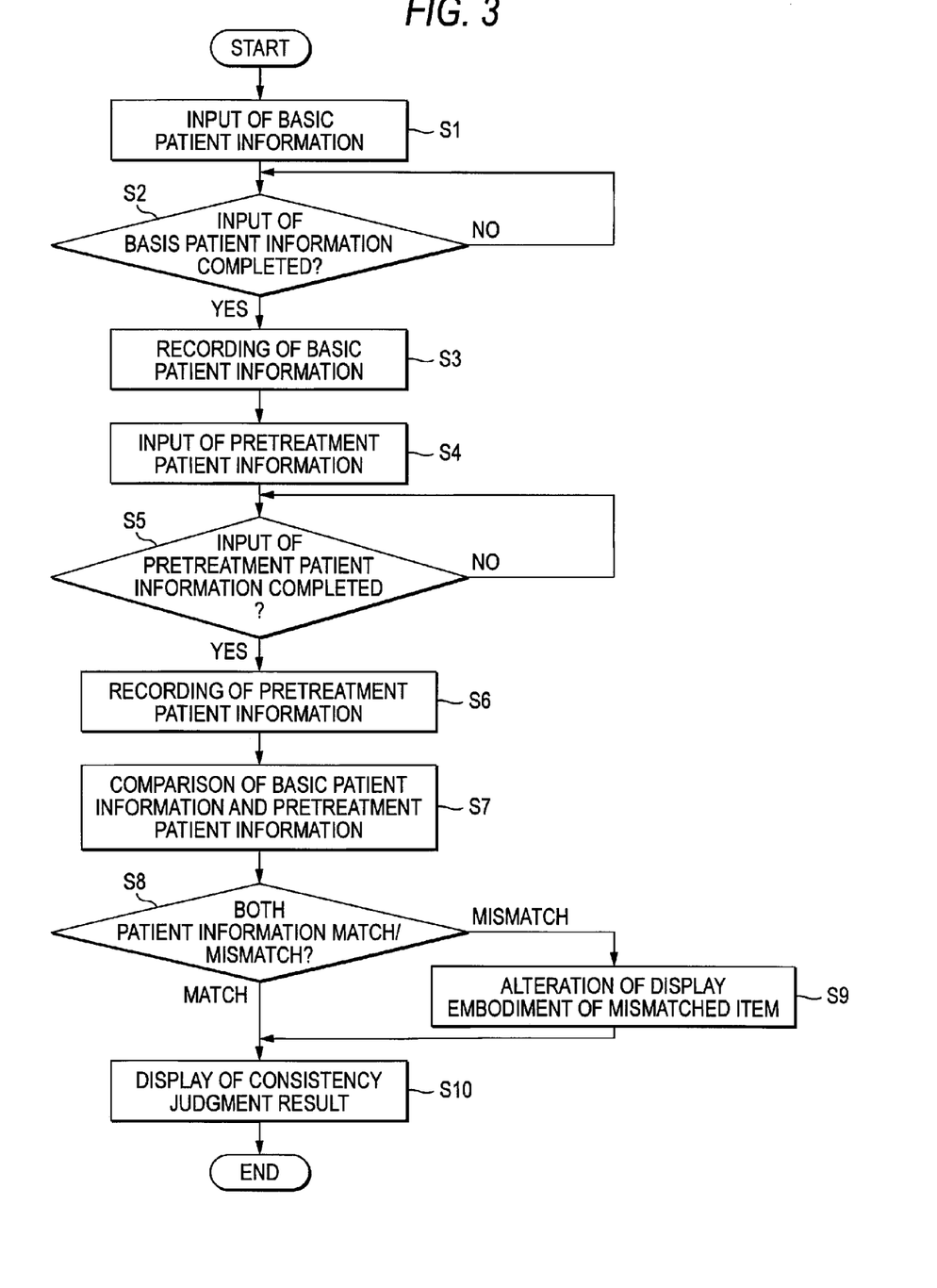
FIG. 3 is a flow chart of the medical service support system of FIG. 1.

FIG. 3 is a flow chart of the medical service support system 1. Firstly, a medical examination of a patient is carried out at an out-patient medical examination section, and inspections necessary for the patient is ordered based on the examination results. Thereafter, the patient information obtained during the medical examination is inputted in the PC 2 of the medical examination section (first input unit) (Step S1).

Figure 4:
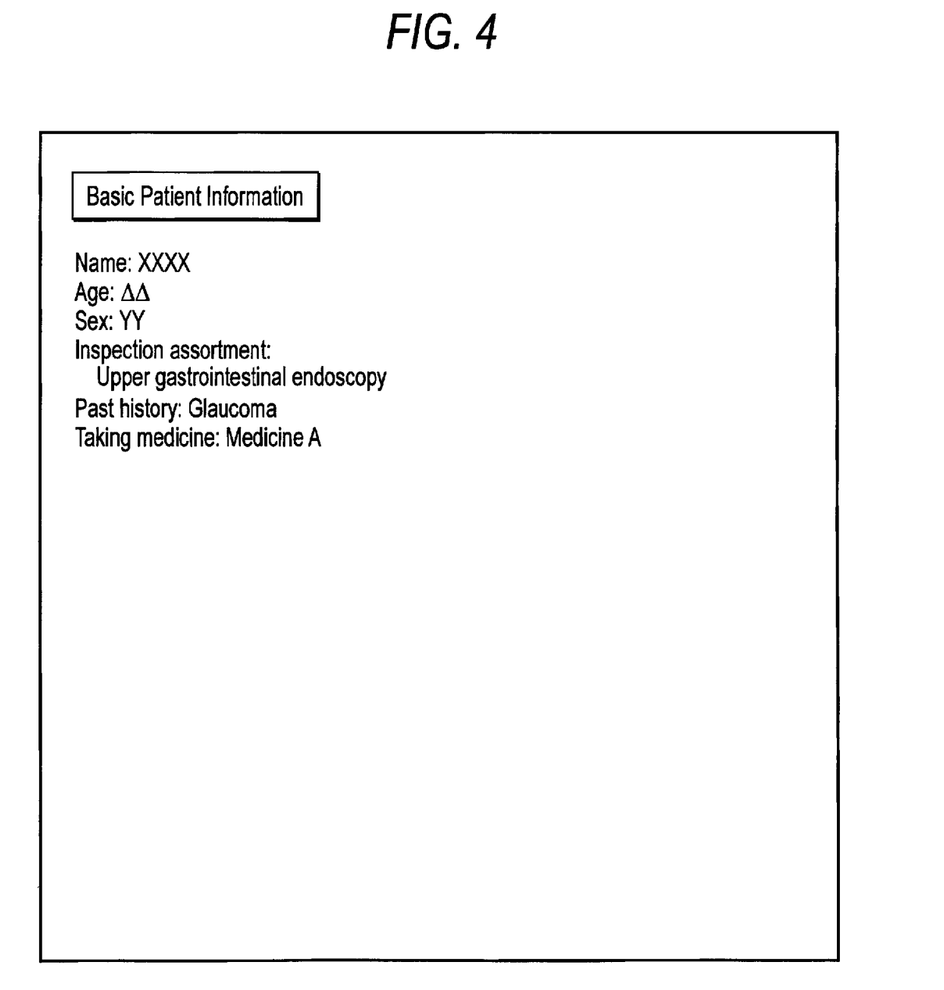
FIG. 4 is a view showing an example of the display by the display unit of PC of the medical examination section of FIG. 1.

An example of the display by the display unit of PC of the medical examination section is shown in FIG. 4, wherein name, age and sex of the patient and assortment of the inspection ordered based on the medical examination results are inputted in the PC 2 as the patient information, his or her past history and taking medicines as a part of the medicine taking information are also inputted therein, and these are displayed in the display unit 12.

When the above-mentioned patient information input is completed (Step S2), the PC 2 of the medical examination section transmits the inputted patient information to the memory 4 via the network 3 and records it as a basic patient information (first patient information) in the patient information data base 21 of memory 4 (Step S3).

Next, a pretreatment of the ordered inspection is executed to the patient. When the pretreatment is carried out, verification of the basic patient information obtained by the out-patient medical examination is generally carried out, verification of identity of the patient is carried out based on his or her name, age, sex and the like, and verification of past history and taking medicines are also carried out. In addition, submission of a written agreement on the inspection is verified, and when food and drink on the day and taking medicines of the patient interfere with the inspection, instructions on the prohibition of food and drink on the day and suspension of medicine taking are given at the time of medical examination, and whether or not these instructions are kept, namely, the presence or absence of food and drink on the day and the number of days of suspended medicine taking, are also verified. Subsequently, a pretreatment such as administration of a predetermined medicine is carried out in accordance with the instructions of the doctor who ordered the inspection, an inspection manual and the like. Thereafter, the patient information obtained at the time of carrying out the pretreatment is inputted in the PC 2 of the pretreatment and inspection section (second input unit) (Step S 4).

Figure 5:
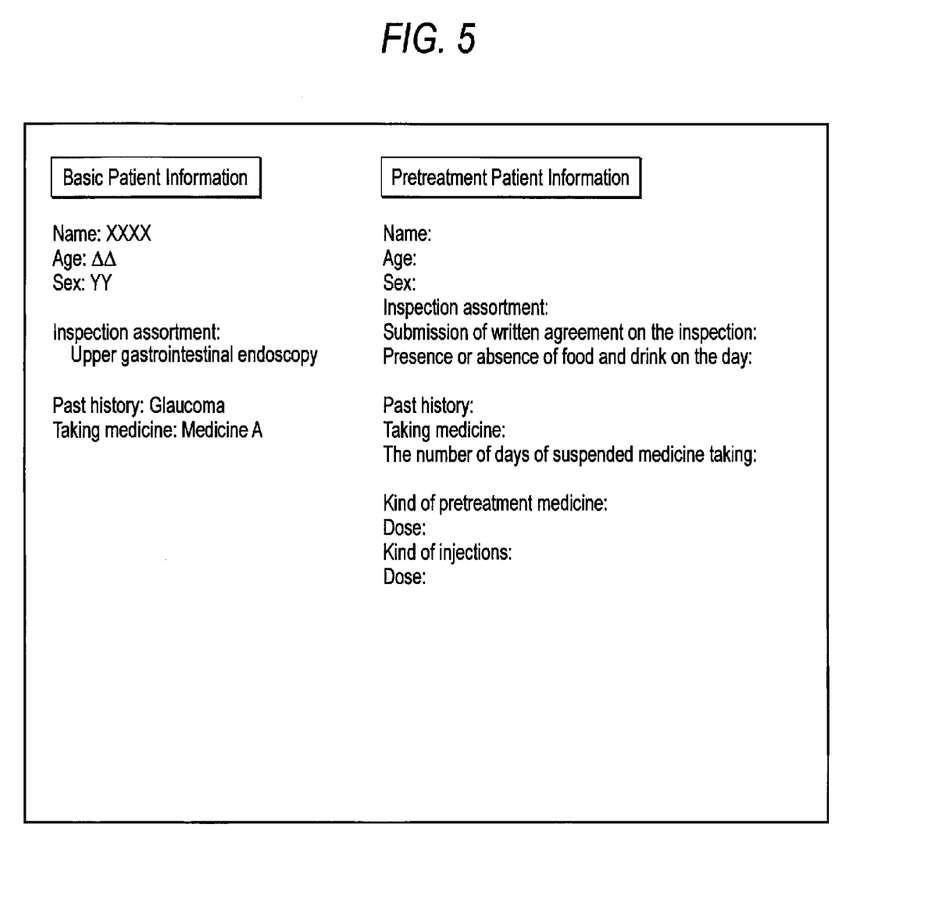
FIG. 5 is a schematic view showing an example of the display by the display unit of PC of the pretreatment and inspection section of FIG. 1.

An example of the display by the display unit of PC of the pretreatment and inspection section is shown in FIG. 5, wherein name, age and sex of the patient, assortment of the inspection, the presence or absence of submission of a written agreement on the inspection, the presence or absence of eating and drinking on the day, past history, taking medicines as the medicine taking information and the number of days of suspended medicine taking and the pretreatment information are inputted in the PC 2 as the patient information, and these are displayed in the display unit 12. As the pretreatment information, kinds of pretreatment medicines, kinds of injections and their doses are included. In this connection, it is desirable that the presence or absence of submission of a written agreement on the inspection, past history, taking medicines, the number of days of suspended medicine taking and the like relatively important items are displayed by an attention-drawing embodiment by which their difference from other items becomes definite, such as bold letters, changed font, changed color, superimpose and the like.

When the above-mentioned patient information input is completed (Step S5), the PC 2 of the pretreatment and inspection section transmits the inputted patient information to the memory 4 via the network 3 and records it as a pretreatment patient information (second patient information) in the patient information data base 21 of the memory 4 (Step S6).

In this connection, in the example shown in FIG. 5, basic patient information is also displayed in the display unit 12 of PC 2 of the pretreatment and inspection section. When ID of the patient is inputted in the PC 2 of the pretreatment and inspection section, the PC 2 reads-in the basic patient information of the patient from the patient information data base 21 of the memory 4 via the network 3. Thereafter, the PC 2 displays the read-in basic patient information in the display unit 12 and displays each item of the pretreatment patient information by a blank space adjoining to the basic patient information to press input of these items. By the joint display of basic patient information, match or mismatch of each item of the common items contained in both of the basic patient information and pretreatment patient information can be recognized at once by a person who inputs the pretreatment patient information, so that when the past history, taking medicines and the like items are mismatch for example, a chance of handing over the result to the doctor who carries out the inspection is provided. By this, execution of proper inspection becomes possible.

Next, an inspection is executed to the patient, and in executing the inspection, whether or not the inspection can be executed is judged by the doctor based on the patient information so far obtained. Illustratively, the PC 2 of the pretreatment and inspection section reads-in the basic patient information and pretreatment patient information which correspond to the inputted ID, from the patient information data base 21 of the memory 4 via the network 3. Thereafter, the PC 2 compares each item of both of the patient information, regarding the common items contained in both of the read-in patient information (Step S7). When there are mismatched items in both of the patient information as a result of comparing each item of the common items in both of the patient information (Step S8), the display embodiment of such items are treated in such a manner that it becomes different from the display embodiment of their complementary items (Step S9), and the result of consistency judgment is displayed in the display unit 12 (Step S10).

Figure 6:
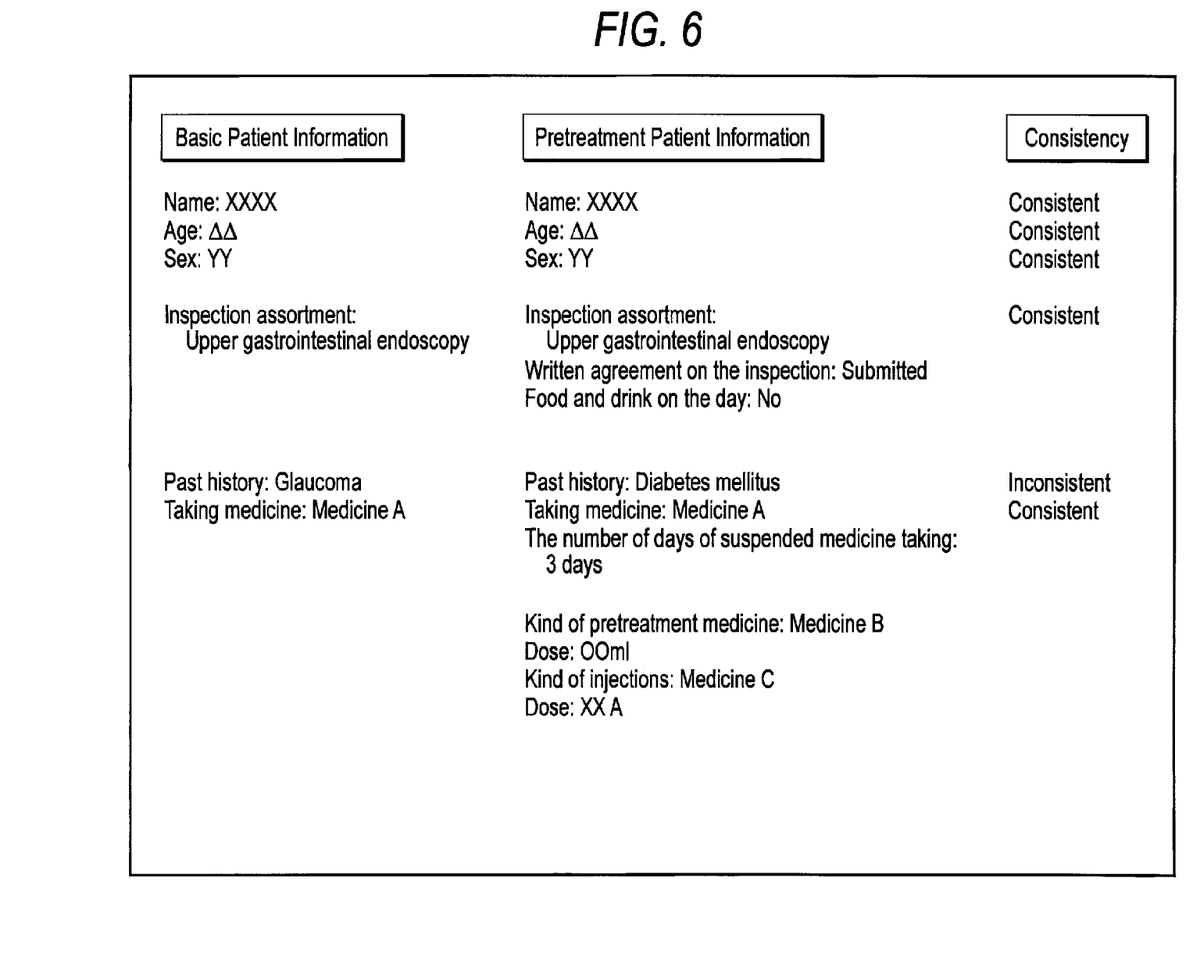
FIG. 6 is a schematic view showing an example of the display by the display unit of the medical examination section of FIG. 1.

An example of the display of consistency judgment result by a display unit is shown in FIG. 6, wherein "match" or "mismatch" is displayed on the display unit 12 as the display unit of the PC 2 of the pretreatment and inspection section, for each item of the basic patient information and pretreatment patient information and common items between both of the patient information. Also, each mismatched item and its "mismatch" are displayed by attention-drawing bold letters. In this connection, in addition to the bold letters, these may be displayed by an embodiment by which their difference from other items becomes distinct, such as change of font, change of color, use of superimpose and the like.

In the example shown in FIG. 6, the item of past history is regarded as mismatch based on the basic patient information and pretreatment patient information, thus awakening attention of the doctor who judges whether or not the inspection should be carried out. Particularly, since the mismatched item between both patient information and the display embodiment of its "mismatch" are different from other items, further more awakening of attention is effected. The doctor who judges whether or not the inspection should be carried out is provided with a chance of asking a patient about which of the basic patient information and pretreatment patient information is correct on, for example, the past history of the patient; and of judging whether or not the pretreatment executed for the verified past history is proper. By this, execution of proper inspection becomes possible.

Next, a modified example of the medical service support system 1 is described. After execution of an inspection to a patient, the inspection information is inputted in the PC 2 of the pretreatment and inspection section, and the PC 2 records the inputted inspection information in the patient information data base 21 of the memory 4 via the network 3. The inspection information recorded in the patient information data base 21 in this way is displayed on the display unit 12 in the next time of inspection as previous inspection information, together with the basic patient information and pretreatment patient information obtained at that time and the consistency judgment result of both of the patient information.

Figure 7:
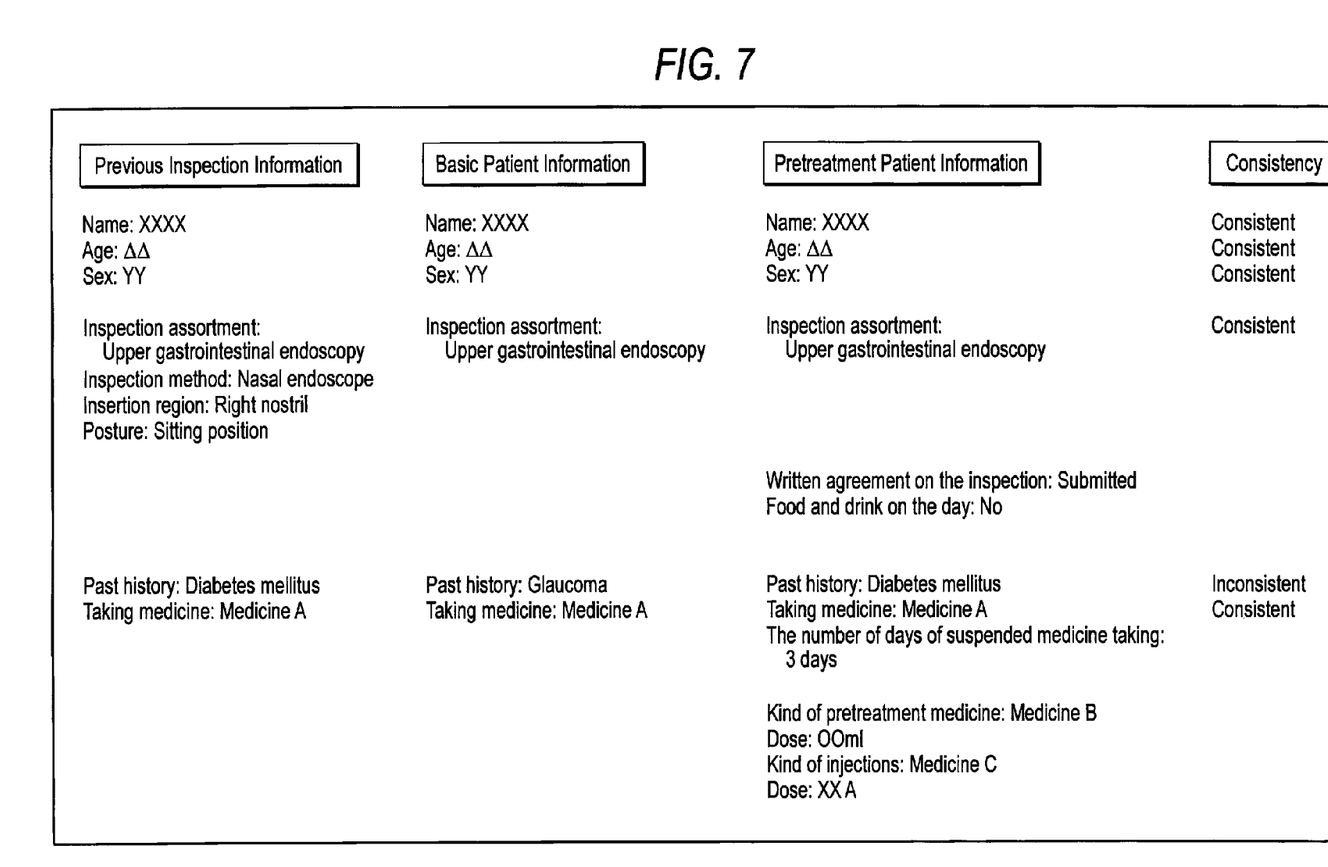
FIG. 7 is a schematic view showing an example of the display by the display unit of a modified example of the medical examination section of FIG. 1.

An example of the display by a display unit is shown in FIG. 7, wherein name, age and sex of the patient, assortment of the inspection and detailed information on the inspection are displayed on the display unit 12 of PC 2 as the display unit of the pretreatment and inspection section, as previous inspection information. As detailed information on the inspection, inspection method, inserting region and posture are displayed. Thus, since previous inspection information is displayed together with the basic patient information and pretreatment patient information and the consistency judgment result of both of the patient information, a doctor can judge whether or not the inspection should be carried out, based on further many patient information. By this, execution of proper inspection becomes possible. In this connection, the inspection information to be displayed as the previous inspection information may be the most recent inspection information but is desirably the inspection information on an inspection identical to the inspection to be carried out now, and in that case, the PC 2 is set such that it retrieves those which coincide with the inspection assortment of pretreatment inspection information from the patient information data base 21 of the memory 4 and displays the results.

Thus, according to the medical service support system 1, consistency judgment results of the basic patient information and pretreatment patient information are displayed so that attention of the person who carries out the inspection can be awakened. By this, proper execution of the inspection becomes possible.

Figure 8:
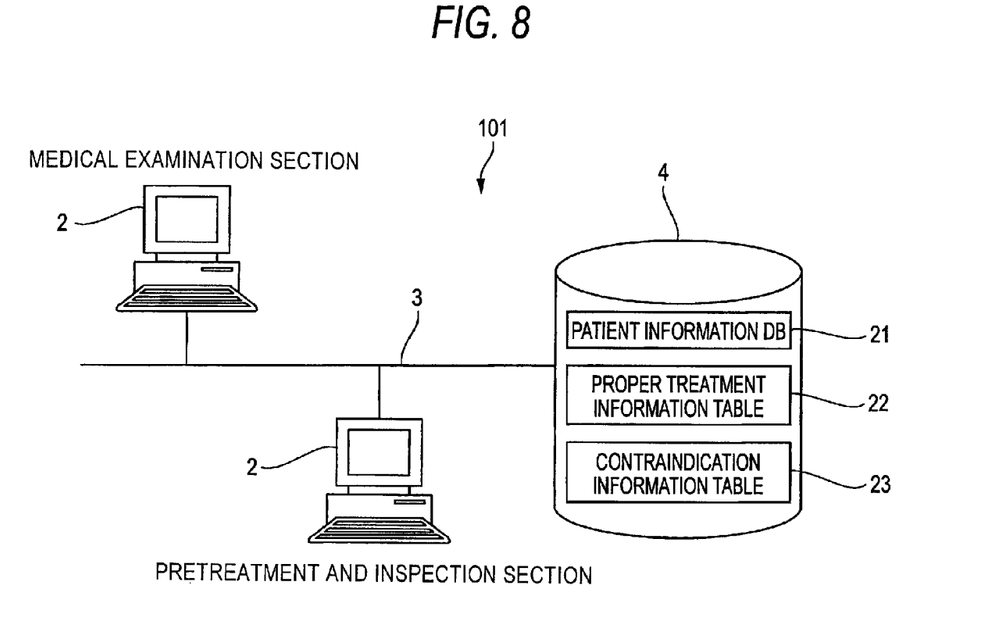
FIG. 8 is a block diagram showing schematic construction of another example of the medical service support system, for use in the explanation of an embodiment of the invention.

FIG. 8 is a block diagram showing schematic construction of another example of the medical service support system, for use in the explanation of the embodiment of the invention. In this connection, descriptions of the elements which are in common with the above-mentioned medical service support system 1 are omitted or simplified by adding the same reference numerals.

As shown in FIG. 8, the medical service support system 101 is equipped with respective PC 2 in the medical examination section and pretreatment and inspection section and is equipped with a memory 4 which is connected with these PC 2 via a net work 3.

The memory 4 further stores a proper treatment information table 22 and a contraindication information table 23. The proper treatment information table 22 keeps proper treatment information for each inspection assortment in the pretreatment of inspection in answer to each disease name, and the contraindication information table 23 keeps contraindication information on medicines in answer to each inspection assortment.

Figure 9:
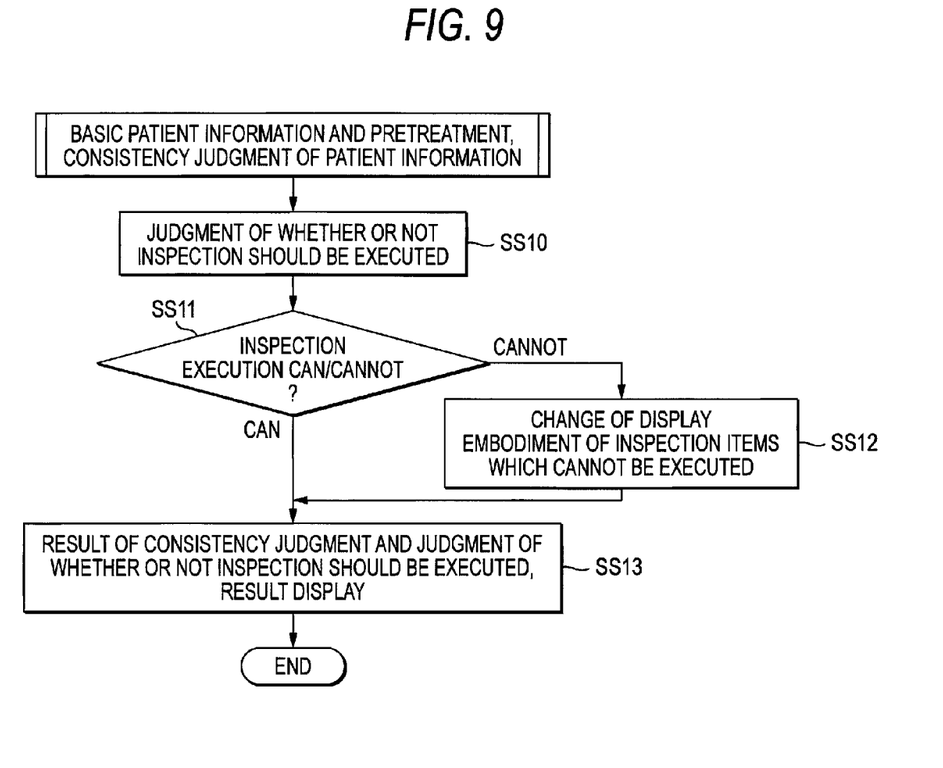
FIG. 9 is a flow chart of the medical service support system of FIG. 8.

FIG. 9 is a flow chart of the medical service support system 101. In this connection, the treatments of Steps S1 to S9 in the above-mentioned medical service support system 1 (recording of the basic patient information which is inputted at the time of medical examination, recording of the pretreatment patient information which is inputted at the time of pretreatment, and consistency judgment of the recorded both patient information) are also carried out in the same manner as in the medical service support system 101. In the following, treatments of in and after consistency judgment of the basic patient information and pretreatment patient information are described.

As shown in FIG. 9, the PC 2 of the pretreatment and inspection section reads-in the basic patient information and pretreatment patient information which correspond to the inputted ID, from the patient information data base 21 of the memory 4 via the network 3, and judges match or mismatch of respective items by comparing each item of both of the patient information, regarding the common items contained in both of the read-in patient information. Also, the PC 2 judges whether or not the inspection should be carried out based on the consistency judgment result and pretreatment patient information (Step SS 10).

Illustratively, the PC 2 firstly judges whether or not the inspection should be carried out in the case of the presence of one or more items which were judged mismatch regarding the common items of the basic patient information and pretreatment patient information.

Figure 10:
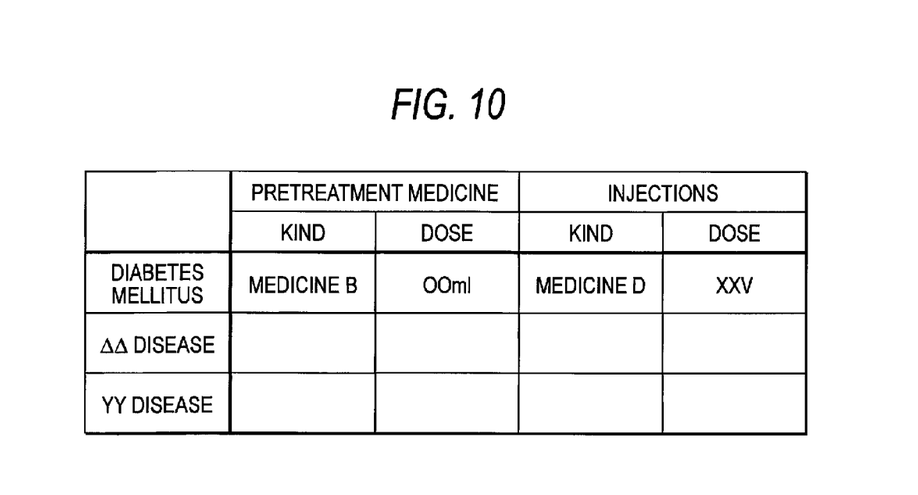
FIG. 10 is a schematic view showing an example of the proper treatment information table of the medical service support system of FIG. 8.

Also, the PC 2 judges whether or not the inspection should be carried out based on the past history of pretreatment patient information by referring to a proper treatment information table 22 of memory 4 via the network 3. An example of the proper treatment information table 22 is shown in FIG. 10. In the illustrated example, a disease name for which a medicine different from the general counterpart is used and proper medicine and its dose for each disease name are kept, regarding the pretreatment medicine and injections to be used in the pretreatment of upper gastrointestinal endoscopy.

The PC 2 retrieves proper treatment information which corresponds to the past history of pretreatment patient information, by referring to the proper treatment information table 22, and when the corresponding proper treatment information is present, judges whether or not the pretreatment information of pretreatment patient information comes under the proper treatment information. For example, when the pat history of pretreatment patient information is diabetes mellitus, the PC 2 retrieves proper pretreatment information which corresponds to diabetes mellitus and compares kind and dose of proper diabetes mellitus pretreatment medicine, and kind and dose of injections and kind and dose of the pretreatment medicine of pretreatment information, and kind and dose of the injections, respectively.

Also, when the pretreatment information comes under the proper treatment information, namely when all items coincide, the PC 2 judges that the inspection can be carried out, and when the pretreatment information does not come under the proper treatment information, namely when there are one or more incompatible items, it judges that the inspection cannot be carried out. In this connection, when the proper treatment information corresponding to the past history of pretreatment patient information is not present in the proper treatment information table 22, the PC 2 judges that the inspection can be carried out.

Figure 11:
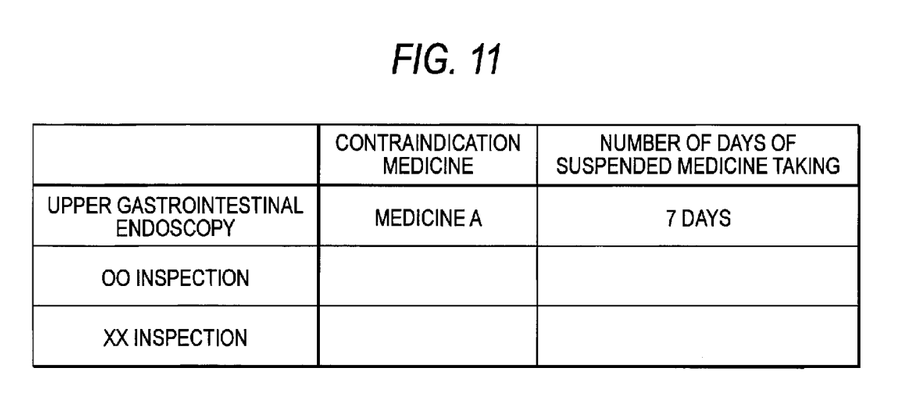
FIG. 11 is a schematic view showing an example of the contraindication information table of the medical service support system of FIG. 8.

In addition, the PC 2 judges whether or not the inspection should be carried out based on the medicine taking information of pretreatment patient information by referring to a contraindication information table 23 of memory 4 via the network 3. An example of the contraindication information table 23 is shown in FIG. 11. In the illustrated example, a fact that taking of a certain medicine within predetermined days before the inspection is a contraindication in the upper gastrointestinal endoscopy, namely the contraindication medicine and the number of days necessary at the least for suspending medicine taking, is kept.

The PC 2 retrieves contraindication information which corresponds to the inspection assortment of pretreatment patient information, by referring to the contraindication information table 23, and when the corresponding proper treatment information is present, judges whether or not the medicine taking information of pretreatment patient information comes under the contraindication information. For example, when the inspection assortment of pretreatment patient information is upper gastrointestinal endoscopy, the PC 2 retrieves contraindication information which corresponds to upper gastrointestinal endoscopy and compares contraindication medicine of the upper gastrointestinal endoscopy and the number of days necessary at the least for suspending taking of the medicine, and taking medicine of the medicine taking information and the number of days for suspending taking of the medicine, respectively.

Also, when the medicine taking information does not come under the contraindication information, namely when the taking medicine of medicine taking information does not coincide with the contraindication medicine of contraindication information, or when the taking medicine of medicine information coincides with the contraindication medicine of contraindication information but the number of days for suspending medicine taking of taking information is equal to or more than the number of days necessary at the least of contradiction information, the PC 2 judges that the inspection can be carried out, and when the medicine taking information comes under the contraindication information, namely, when the taking medicine of medicine taking information coincides with the contraindication medicine of contraindication information and the number of days for suspending medicine taking of taking information is less than the number of days necessary at the least of contradiction information, it considers that the medicine taking information comes under the contraindication information and therefore judges that the inspection cannot be carried out. In this connection, when the contraindication information which corresponds to the inspection assortment of pretreatment patient information of is not present in the contraindication information table 23, the PC 2 judges that the inspection can be carried out.

As described in the above, the PC 2 judges whether or not an inspection should be carried out, and as a result, when there are items which were judged that the inspection should not be carried out (Step SS 11), treats these items in such a manner that their displaying modes become different from the displaying modes of their complementary items (Step SS 12) and displays result of the judgment of whether or not the inspection should be carried out on the display unit 12 together with result of the consistency judgment (Step SS 13).

Figure 12:
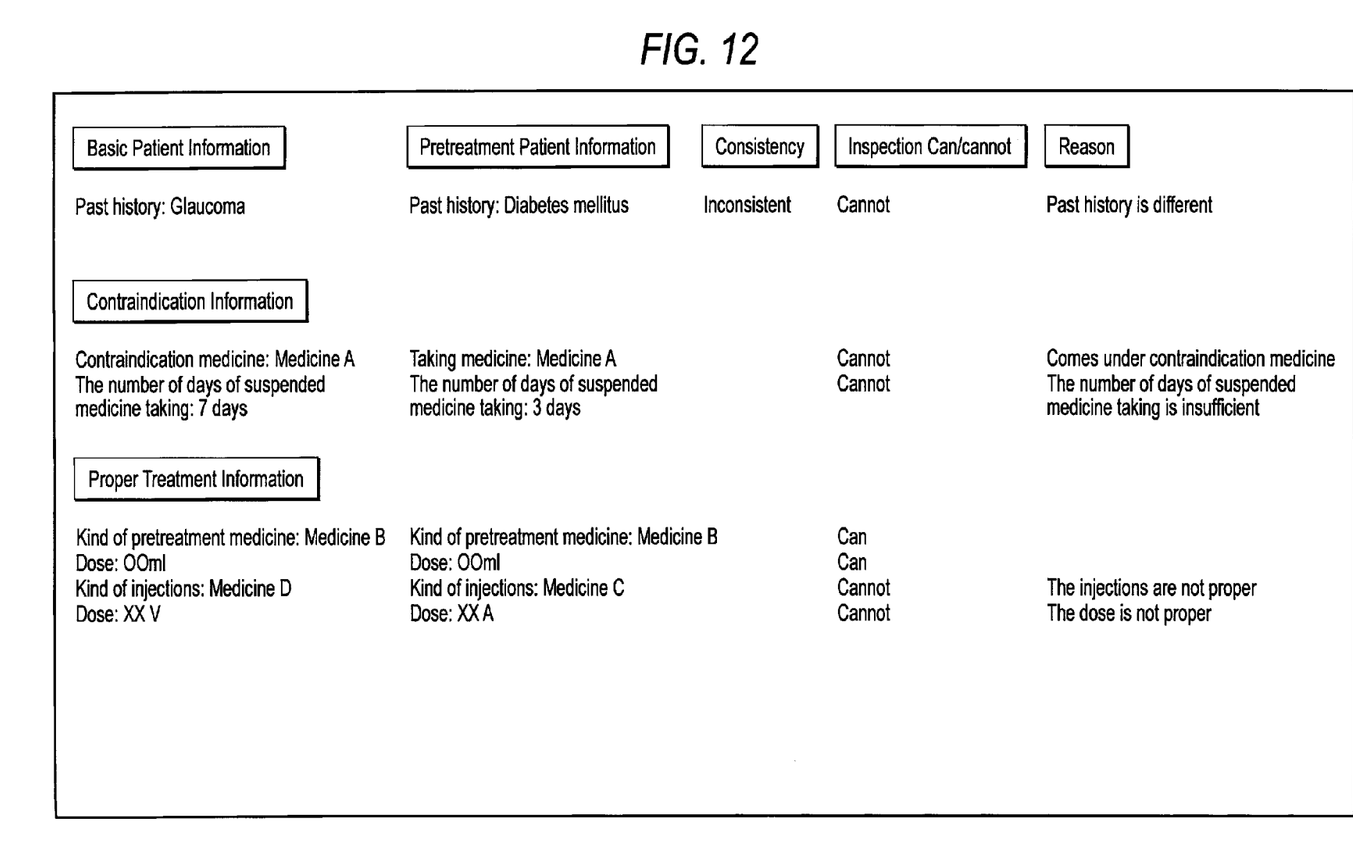
FIG. 12 is a schematic view showing an example of the display by the display unit of the medical examination section of FIG. 8.

An example of display of the result of judgment of whether or not the inspection should be carried out by the display unit is shown in FIG. 12. Regarding the common items between basic patient information and pretreatment patient information, both of the patient information of inconsistent items and their "inconsistency" alone are displayed. According to this, inconsistent items among the common items between basic patient information and pretreatment patient information are as clear as daylight and are helpful in awakening attention of the doctor who carry out the inspection.

Also, regarding the result of judgment of whether or not the inspection should be carried out, "yes" or "no" is displayed for each item of the pretreatment patient information. In addition, items of no inspection execution and their "no" are displayed by bold letters for drawing attention. In this connection, in addition to the bold letters, these may be displayed by an embodiment by which their difference from other items becomes distinct, such as change of font, change of color, use of superimpose and the like.

In the example shown in FIG. 12, the taking medicine A of pretreatment patient information coincides with the contraindication medicine A of contraindication information and the number of days for suspension of medicine taking of pretreatment patient information, 3 days, is less than the number of days for suspension of medicine taking of contraindication information, 7 days, so that the judgment of no inspection execution is made by considering that the medicine taking information comes under the contraindication information, and "no" is displayed on these items. In addition, the injections C of pretreatment patient information does not coincide with the injections D of proper treatment information and their doses do not coincide too, so that the judgment of no inspection execution is made by considering that the pretreatment information comes under the proper treatment information, and "no" is displayed on these items.

In addition, in the example shown in FIG. 12, the reasons why judged as no inspection execution are also displayed. For example, in the judgment of whether or not an inspection should be carried out based on the past history of pretreatment information, the reasons are displayed by relating reasons in advance to respective items of the proper treatment information kept in proper treatment information table 22 and extracting the reasons related to the items having incompatible pretreatment information. The joint display of reasons why judged as no inspection execution is particularly useful when whether or not the inspection should be carried out is displayed by "yes" or "no" as a whole.

Thus, according to the medical service support system 101, whether or not an inspection should be carried out is judged based on the consistency judgment result of basic patient information and pretreatment patient information and the pretreatment patient information, so that artificial errors in judging whether or not the inspection should be carried out can be avoided. By this, proper execution of the inspection becomes possible.

According to the above described exemplary embodiments, proper execution of inspections becomes possible by effectively using patient information.

What is claimed is:

1. A medical service support system, comprising:
a first input unit that inputs, in at least one processor, first patient information on a patient in carrying out a medical examination of the patient;
a second input unit that inputs second patient information on the patient in executing, to the patient, a pretreatment of an inspection being ordered according to a medical examination result of the patient;
wherein the second input unit newly inputs for common items contained in both of the first patient information and the second patient information, corresponding data pieces of the second patient information;
a memory that stores the first patient information inputted by the first input unit and the second patient information inputted by the second input unit,
wherein the memory stores for the common items, data pieces of the first patient information and corresponding data pieces of the second patient information;
a consistency judging unit that judges a match or mismatch for the respective common items, by comparing data pieces of the first patient information with data pieces of the second patient information for the respective common items; and
a display unit that displays a consistency judgment result by the consistency judging unit,
wherein, when one of the common items is judged to be matched, data of said one of the common items of the first patient information and corresponding data of said one of the common items of the second patient information are both displayed with an indication of a consistency between the first patient information and the second patient information.

2. The medical service support system according to claim 1, wherein the display unit displays, in a side-by-side manner:
the first patient information;
the second patient information; and
the match or mismatch of the respective common items judged by the consistency judging unit, and
wherein the display unit changes a display mode of an item judged mismatched from a display mode of an item complementary to both of the first patient information and the second patient information.

3. The medical service support system according to claim 1, wherein the display unit only displays items judged mismatched by the consistency judging unit, regarding the common items among the first patient information and the second patient information, and the mismatches.

4. The medical service support system according to claim 1, further comprising:
an inspectability judging unit that judges whether or not the inspection is allowed to be executed, wherein
the inspectability judging unit judges whether or not the inspection is allowed to be executed, in a case of a presence of one or more items judged mismatched by the consistency judging unit, regarding the common items among the first patient information and the second patient information, and
the display unit further displays an inspectability judgment result by the inspectability judging unit.

5. The medical service support system according to claim 4, wherein at least the second patient information includes a past history of the patient and information on the pretreatment,
the memory stores a proper treatment information table which keeps proper treatment information on a pretreatment of an inspection associated with a disease name, the inspectability judging unit retrieves proper treatment information which corresponds to the past history of the second patient information, by referring to the proper treatment information table, and the inspectability judging unit judges whether or not the inspection is allowed to be executed when the pretreatment information of the second patient information does not come under the retrieved proper treatment information.

6. The medical service support system according to claim 4, wherein at least the second patient information includes medicine taking information of the patient and a kind of the inspection, the memory stores a contraindication information table which keeps contraindication information on a drug associated with the kind of the inspection, the inspectability judging unit retrieves contraindication information which corresponds to the kind of inspection of the second patient information, by referring to the contraindication information table, and the inspectability judging unit judges whether or not the inspection is allowed to be executed when the medicine taking information of the second patient information comes under the retrieved contraindication information.

7. The medical service support system according to claim 1, wherein the memory stores information on at least one of inspections executed in the past to the patient, and wherein the display unit further displays the inspection information recorded in the memory.

8. The medical service support system according to claim 1, wherein the consistency judgment result displayed in the display unit comprises displaying the match or the mismatch for each item of the first patient information and the second patient information with respect to the common items contained in both of the first patient information and the second patient information.

9. The medical service support system according to claim 1, wherein, each of the data of said one of the common items of the first patient information and the corresponding data of said one of the common items of the second patient information, which are displayed in the display unit, includes an inspection assortment of the patient and a past medical history of the patient.

10. A non-transitory computer readable medium storing a program causing a computer to execute a process for supporting medical service, the process comprising:

storing in a memory, first patient information which is inputted in carrying out a medical examination of a patient;

storing in the memory, a second patient information which is inputted in executing, to the patient, a pretreatment of an inspection ordered according to a medical examination result, wherein the storing includes storing newly common items contained in both of the first patient information and the second patient information, corresponding data pieces of the second patient information;

judging a match or mismatch for the respective common items, by comparing data pieces of the first patient information with data pieces of the second patient information for each the respective common items; and displaying a consistency judgment result by the judging, wherein the memory stores for the common items, data pieces of the first patient information and corresponding data pieces of the second patient information, and wherein, when one of the common items is judged to be matched, data of said one of the common items of the first patient information and corresponding data of said one of the common items of the second patient information are both displayed with an indication of a consistency between the first patient information and the second patient information.

11. The non-transitory computer readable medium for supporting medical service according to claim 10, wherein the displaying includes displaying, in a side-by-side manner:

the first patient information;

the second patient information; and the judged match or mismatch of the respective common items, and wherein the displaying includes changing a display mode of an item judged mismatched from a display mode of an item complementary to both of the first patient information and the second patient information.

12. The non-transitory computer readable medium for supporting medical service according to claim 10, wherein the displaying includes only displaying items judged mismatched, regarding the common items among the first patient information and the second patient information, and the mismatches.

13. The non-transitory computer readable medium for supporting medical service according to claim 10, the process further comprising:

judging whether or not the inspection is allowed to be executed, wherein a judgment as to whether or not the inspection is allowed to be executed is performed, in a case of a presence of one or more items judged mismatched, regarding the common items among the first patient information and the second patient information, and the displaying includes displaying an inspectability judgment result of the judgment as to whether or not the inspection is allowed to be executed.

14. The non-transitory computer readable medium for supporting medical service described in claim 13, wherein at least the second patient information includes a past history of the patient and information on the pretreatment, wherein the memory stores a proper treatment information table which keeps proper treatment information on the pretreatment of an inspection associated with a disease name, and wherein the process further comprises:

retrieving proper treatment information which corresponds to the past history of the second patient information, by referring to the proper treatment information table; and the judgment as to whether or not the inspection is allowed to be executed is performed when the pretreatment information of the second patient information does not come under the retrieved proper treatment information.

15. The non-transitory computer readable medium for supporting medical service according to claim 13, wherein at least the second patient information includes medicine taking information of the patient and a kind of the inspection, and wherein the memory stores a contraindication information table which keeps contraindication information on a drug associated with the kind of the inspection, the process further comprises retrieving contraindication information which corresponds to the kind of inspection of the second patient information, by referring to the contraindication information table, and the judgment as to whether or not the inspection is allowed to be executed is performed when the medicine taking information of the second patient information comes under the retrieved contraindication information.

16. The non-transitory computer readable medium for supporting medical service according to claim 10, wherein the memory stores information on at least one of inspections executed in the past to the patient, and
    the displaying includes displaying the inspection information recorded in the memory.

17. The non-transitory computer readable medium for supporting medical service according to claim 10, wherein said displaying the consistency judgment result comprises displaying the match or the mismatch for each item of the first patient information and the second patient information with respect to the common items contained in both of the first patient information and the second patient information.

18. The non-transitory computer readable medium for supporting medical service according to claim 10, wherein each of the data of said one of the common items of the first patient information and the corresponding data of said one of the common items of the second patient information, which are displayed, includes an inspection assortment of the patient and a past medical history of the patient.

* * * * *